United States Patent [19]

Rosenbrook, Jr.

[11] 4,330,673
[45] May 18, 1982

[54] PROCESS FOR PRODUCING 3-O-DEMETHYLAMINOGLYCOSIDE AND NOVEL 3-O-DEMETHYLFORTIMICIN DERIVATIVES

[75] Inventor: William Rosenbrook, Jr., Libertyville, Ill.

[73] Assignee: Abbott Laboratories, Chicago, Ill.

[21] Appl. No.: 126,731

[22] Filed: Mar. 3, 1980

Related U.S. Application Data

[63] Continuation-in-part of Ser. No. 25,238, Mar. 29, 1979, Pat. No. 4,230,848.

[51] Int. Cl.³ .............................................. C07H 15/22
[52] U.S. Cl. .................................... 536/16.1; 424/180
[58] Field of Search ............................. 536/17 B, 17 R

[56] References Cited

U.S. PATENT DOCUMENTS

| | | | |
|---|---|---|---|
| 4,124,756 | 11/1978 | Martin et al. | 536/17 B |
| 4,176,178 | 11/1979 | Martin et al. | 536/17 B |
| 4,187,297 | 2/1980 | Martin et al. | 536/17 B |

Primary Examiner—Johnnie R. Brown
Attorney, Agent, or Firm—Robert L. Niblack; Gildo E. Fato; Joyce R. Niblack

[57] ABSTRACT

An improved process for producing 3-O-demethylfortimicins and other O-methyl-containing aminoglycoside antibiotics comprising the steps of reacting the fortimicin to be 3-O-demethylated with a borontrihalide and recovering the 3-O-demethylfortimicin from the reaction mixture. 3-O-Demethylfortimicin derivatives which can be prepared by this process include compounds represented by the formula:

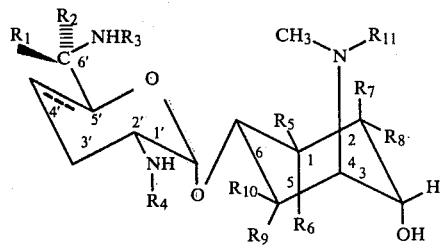

wherein: $R_1$ and $R_2$ are hydrogen or methyl with the limitation that one of either $R_1$ or $R_2$ must be hydrogen; $R_3$ is hydrogen or methyl; $R_4$ and $R_{11}$ are the same or different members of the group consisting of hydrogen, acyl, aminoacyl, diaminoacyl, N-loweralkylaminoacyl, N,N-diloweralkylaminoacyl, hydroxy-substituted aminoacyl, loweralkyl, aminoloweralkyl, diaminoloweralkyl, hydroxyloweralkyl, N-loweralkylaminoloweralkyl, N,N-diloweralkylaminoloweralkyl, N-loweralkylaminohydroxyloweralkyl and N,N-diloweralkylaminohydroxyloweralkyl; $R_5$ and $R_6$ are hydrogen or amino with the limitation that one of either $R_5$ and $R_6$ must be hydrogen; $R_7$ and $R_8$ are selected from the group consisting of either hydrogen, hydroxy, amino and chloro with the limitation that one of either $R_7$ or $R_8$ must be hydrogen; $R_9$ and $R_{10}$ are hydrogen or hydroxy with the limitation that one of either $R_9$ or $R_{10}$ must be hydrogen; and the pharmaceutically acceptable salts thereof. Compounds other than those wherein $R_1$ is hydrogen, $R_2$ is methyl, $R_3$ is hydrogen, $R_5$ is amino, $R_8$ is hydroxy and $R_{10}$ is hydroxy when $R_{4'}-R_{5'}$ is saturated, are novel and are useful as antibiotics, antibacterial agents, and as intermediates for producing other useful fortimicin derivatives.

43 Claims, No Drawings

PROCESS FOR PRODUCING 3-O-DEMETHYLAMINOGLYCOSIDE AND NOVEL 3-O-DEMETHYLFORTIMICIN DERIVATIVES

CROSS REFERENCE TO RELATED APPLICATIONS

This application is a continuation-in-part of copending U.S. patent application Ser. No. 025,238, filed Mar. 29, 1979, now U.S. Pat. No. 4,230,848.

BACKGROUND OF THE INVENTION

The aminoglycoside antibiotics are a valuable therapeutic class of antibiotics which include the kanamycins, gentamicins, streptomycins and the more recently discovered fortimicins. While the naturally produced parent antibiotics are, in themselves, valuable therapeutic entities, chemical modifications have been found to improve the activity, either intrinsic or against resistant strains of organisms, or to reduce the toxicity of the parent antibiotics. And, because of the development of aminoglycoside-resistant strains and inactiviation of the parent antibiotics by R-mediated factors which can develop, the search continues for new entities.

One such entity has been discovered in the fortimicin family of antibiotics, 3-O-demethylfortimicin A. The corresponding 3-O-demethylfortimicin B is also of interest. The 3-O-demethylfortimicins are disclosed in U.S. Pat. No. 4,124,756. Certain 4-N-, and 2'-N-acyl and alkyl derivatives are disclosed in allowed, commonly assigned, U.S. Pat. No. 4,187,297. 2-Deoxy-3-O-demethyl Fortimicins are disclosed in commonly assigned, co-pending U.S. Ser. No. 079,132 filed Sept. 26, 1979, now U.S. Pat. No. 4,251,516.

Previously known methods for producing 3-O-demethylfortimicin A and 3-O-demethylfortimicin B have resulted in such low yields that production of these antibiotics was extremely slow and inefficient, and there has been a need for improved methods of O-demethylating, O-methyl-containing compounds. The present invention provides one such method as well as novel 3-O-demethyl fortimicins derivatives.

SUMMARY

The present invention provides an improved process for synthesizing 3-O-demethylfortimicins directly from the parent antibiotics and comprises the steps of reacting the fortimicin to be O-demethylated with a boron trihalide, preferably boron tribromide in the presence of an inert solvent, i.e., a halogenated hydrocarbon or hydrocarbon solvent such as methylene chloride which provides solubility for the fortimicins, removal of the solvent and residual boron trihalide and isolation of the desired product by chromatography.

DETAILED DESCRIPTION OF PREFERRED EMBODIMENTS

For illustrative purposes, this invention will be exemplified by the O-demethylation of fortimicin A, fortimicin B and a number of other representative fortimicin derivatives, in some instances, to provide novel fortimicin derivatives. Generally speaking, in the practice of the preferred embodiment of this invention, to obtain a 3-O-demethylfortimicin, for example, 3-O-demethylfortimicin A, in approximately thirty percent yield, fortimicin A free base is dissolved in methylene chloride, preferably in an amount of from about 1.0 to about 100 mg (0.0025 to 0.25 mmole) of fortimicin A free base to each ml of an inert solvent such as methylene chloride, and the reaction mixture is cooled to a temperature of from about −72° to about 4° C., preferably about 0° C. and treated with from about 10 to about 100 equivalents of a boron trihalide selected from the group consisting of boron tribromide, boron trichloride and boron triiodide with stirring for about 10 to about 60 minutes, preferably for about 30 minutes at a temperature of from about −72° to about 30° C., preferably at about 0° C.

Solvent and residual boron trihalide are then removed in vacuo at a temperature of from about 30° to about 60° C., the remaining reaction mixture treated with an appropriate solvent such as methanol to remove any remaining solvent and boron trihalide and then evaporated to a residue, preferably in vacuo, at a temperature of from about 30° to about 60° C. It is then preferred to carry out the latter step twice.

3-O-Demethylfortimicin A is then isolated by silica gel chromatography using an appropriate solvent system such as methylene chloride-methanol-concentrated ammonia in a 2:3:1(v/v/v) ratio to obtain the product as the free base in approximately thirty percent yield.

3-O-Demethylfortimicin B or a derivative thereof, which are also useful as intermediates in the synthesis of 4-N-acyl and alkyl-3-O-demethylfortimicin B derivatives, can be prepared by reacting fortimicin free base, or a derivative thereof, with a boron trihalide, preferably boron tribromide following the general procedure outlined above for the corresponding fortimicin A derivative. 3-O-demethylfortimicin B is obtained in approximately forty percent yields by the process of this invention.

While it is preferred to first dissolve the fortimicin compound to be demethylated in an inert solvent, demethylation can be effected by reacting the fortimicin with the boron trihalide neat.

The following reaction schemes summarize the process of the present invention.

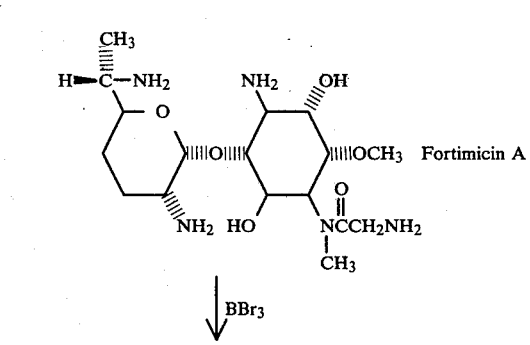

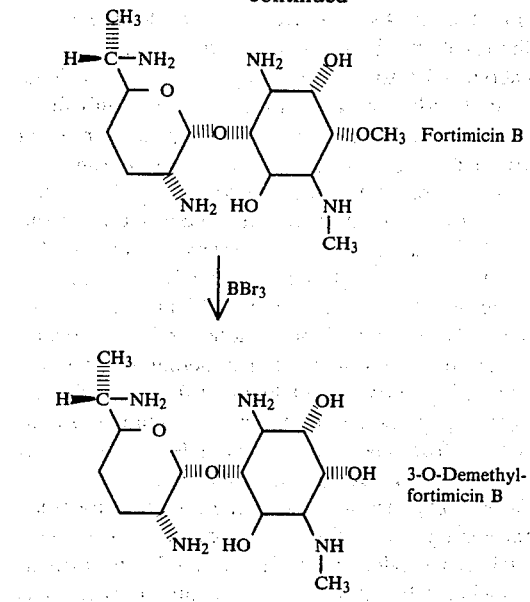

Fortimicin A can be produced according to the method described in U.S. Pat. No. 3,976,768. Fortimicin B can be prepared according to the method described in U.S. Pat. No. 3,931,400.

The solvents and boron trihalides and other materials used in the practice of this invention and are all available from well known commercial sources.

The following examples further illustrate the present invention.

EXAMPLE 1

3-O-Demethylfortimicin A

Fortimicin A free base (400 mg, 0.99 mmole) was dissolved in dry methylene chloride (25 ml) (distilled from calcium hydride and stored over Type A molecular sieve), cooled to 0° C. and treated with boron tribromide (4.6 ml, 50 mmole). The mixture was stirred under a drying tube for 30 minutes at 0° C. and then for 16 hours at room temperature. Solvent and residual boron tribromide were removed in vacuo at 40° C. in a bath. Methanol (20 ml) was added to the reaction mixture and the mixture was evaporated to a residue in vacuo at 40° C. and the step repeated two times.

3-O-Demethylfortimicin A was isolated from the latter residue by silica gel chromatography, using methylene chloride-methanol-concentrated ammonia (2:3:1 v/v/v) as a white foam (116 mg, 30% of theory). Unreacted fortimicin A (164 mg) was also recovered from the chromatography.

EXAMPLE 2

3-O-Demethylfortimicin B

Twenty-five ml of a two percent solution of fortimicin B free base (500 mg, 1.4 mmole) in methylene chloride (stored over Type A molecular sieve) was cooled to 0° C. and treated with boron tribromide (1.3 ml, 3.5 g, 14 mmole). The mixture was stirred under a drying tube for 30 minutes at 0° C. and then for 16 hours at room temperature. Solvent and residual boron tribromide were removed in vacuo at 40° C. (bath). Methanol (20 ml) was added to the reaction mixture and evaporated to a residue in vacuo at 40° C. (bath) and the last step repeated two times.

3-O-Demethylfortimicin B free base (192 mg) was isolated from the latter residue in a 41 percent yield by silica gel column chromatography using methylene chloride-methanol-concentrated ammonia[4:4:1 (v/v/v)] as a white foam. This can be converted into the desired salt, as can be product of Example 1, by titration with the appropriate acid. The hydrochloride salt formed by titration with dilute hydrochloric acid and lyophilization of the resulting solution is identical with that described in U.S. Pat. No. 4,124,756.

While the present invention has, for illustrative purposes, been described in connection with the O-demethylation of fortimicin A and fortimicin B, it has successfully been used to O-demethylate known fortimicin A and B derivatives as well and thus to prepare the O-demethyl derivatives directly, including 3-O-demethyl derivatives of U.S. Pat. No. 4,124,756 and of commonly assigned, U.S. Pat. No. 4,187,297. The process has further resulted in the preparation of novel fortimicin derivatives as well, and the following examples further illustrate the present invention.

EXAMPLE 4

3-O-Demethyl-2,5-dideoxyfortimicin A tetrahydrochloride 2,5-Dideoxyfortimicin A tetrahydrochloride (566 mg, 1.1 mmole), prepared according to U.S. Pat. No. 4,208,407, was taken up in about 5 ml of water and applied to an 8 ml column of Dowex AG 1X-2 resin (OH$^-$ form) and the column eluted with water. The basic elutes were then lypholized to provide 2,5-dideoxyfortimicin A free base (371 mg, 0.99 mmole). The free base was dissolved in about 5 ml of dry methylene chloride and treated with about ½ ml of type 4A molecular sieve er the weekend.

The 2,5-dideoxyfortimicin solution was decanted and the sieve washed with additional dry methylene chloride. The washings were combined with the decanted solution and the resulting 25 ml of solution were placed in a 100 ml ℞.R.B. flask fitted with a magnetic stirrer and drying tube and cooled in an ice bath to about 0° C. Boron tribromide (4.63 ml, 49.5 mmole, 50 equivalents) was added and the mixture stirred at 0° C. for about 30 minutes and overnight at room temperature.

Solvent and residual boron tribromide were removed in vacuo at 40° C. and the mixture was evaporated to a residue in vacuo at 40° C. The step was repeated two times and the 3-O-demethyl-2,5-dideoxyfortimicin A was isolated from the latter by silica gel chromatography and converted to the tetrahydrochloride in twenty one percent yield: M+ obsd. $C_{16}H_{33}N_5O_4$ requires 359.2532, measd. 359.2537; PMR($D_2O$)$\delta$1.77d($C$-$6'$—$CH_3$, $J_{5',6'}=7$ hz), 3.40s(N$CH_3$), 5.76d($C_{1'}$—H,$J_{1',2'}=3.5$)

EXAMPLE 7

3-O-Demethyl-5-deoxyfortimicin A tetrahydrochloride

5-Deoxyfortimicin A tetrahydrochloride (407 mg, 0.760 mmole), prepared according to U.S. Pat. No. 4,208,407 and U.S. Pat. No. 4,207,415 was taken up in about 5 ml of water and applied to an 8 ml column of Dowex AG 2x-8 resin(OH$^-$ form) and the column eluted with water. The basic elutes were then lypholized to provide 5-deoxyfortimicin A(250 mg, 0.642 mmole). The free base was dissolved in about 5 ml of dry methylene chloride and treated with about ½ ml of type 4A molecular sieve overnight.

The solution was decanted from the molecular sieve and the sieve washed with dry methylene chloride. The washings were combined with the decanted solution to provide a final volume of 25 ml. The solution was placed in a 100 ml ℬ.R.B. flask fitted with a magnetic stirrer and drying tube and cooled in an ice bath. Boron tribromide (2.97 ml, 32 mmole, 50 equivalents) was then added and the mixture stirred at about 0° C. for approximately 30 minutes. Solvent and residual boron tribromide were removed from the reaction mixture at 40° C. (bath). Methanol was added to the mixture and the latter removed in vacuo. The latter step was repeated two more times and the product isolated by silica gel chromatography as described in Example 1 and converted to the tetrahydrochloride salt in twenty four percent yield: Mass spec M+ obsd. $C_{16}H_{33}N_5O_5$ requires 375.2482, measd. 359.2490; PMR($D_2O$)$\delta$1.76d(C-6'—$CH_3$, $J_{5',6'}$=6.6 Hz), 3.41s(N$CH_3$), 5.74d($C_{1'}$—H,$J_{1',2'}$=3.0 Hz).

EXAMPLE 6

3-O-Demethyl-2-epi-fortimicin B

A. 1,2',6'-Tri-N-benzyloxycarbonyl-2-epi-fortimicin B-4,5-carbamate

To a magnetically stirred solution of 0.155 g. of 1,2',6'-tri-N-benzyloxycarbonylfortimicin B 4,5-carbamate in 2 ml. of pyridine, cooled in an ice bath, was added 0.42 g. of methanesulfonic anhydride. Stirring was continued with cooling for 1 hour and then at ambient temperature overnight. The resulting mixture was poured into 100 ml. of 5% aqueous $NaHCO_3$. The aqueous suspension was extracted twice with 50 ml. portions of $CHCl_3$. The $CHCl_3$ solutions were combined and washed with 100 ml. of 5% aqueous $NaHCO_3$. The $CHCl_3$ solution was dried over anhydrous $MgSO_4$. Evaporation of the $CHCl_3$ under reduced pressure left 0.169 g of product as a glass: $[\alpha]_D^{21}$—4.24° (c 1%, $CH_3OH$); I.R. ($CDCl_3$) 3440, 3300, 1760, 1708 cm$^{-1}$; NMR ($CDCl_3$) $\delta$1.00 d ($C_6'$—$CH_3$, J=3.6$H_3$); 2.83 (N$CH_3$); 2.99 (OS$O_2CH_3$); 3.52 (O$CH_3$).

Anal. Calcd for $C_{41}H_{50}N_4O_{14}$:C, 57.60; H, 5.90; N, 6.55. Found: C, 58.79; H, 6.28; N, 7.12.

B. 2',6'-Di-N-benzyloxycarbonyl-2-epi-fortimicin B 1,2-[2-benzyloxy]oxazoline 4,5-carbamate A magnetically stirred mixture of 2.0 g. of 1,2,6'-tri-N-benzyloxycarbonyl-2-O-methanesulfonylfortimicin B-4,5-carbamate, 1.22 g. of sodium bicarbonate, 7.4 ml. of water and 29.6 ml. of tetrahydrofuran was heated at 67 degrees for 5 days. The resulting mixture was poured into 500 ml. of 5% aqueous $NaHCO_3$. The aqueous suspension was extracted with two 250-ml. portions of $CHCl_3$. The $CHCl_3$ solutions were combined and dried (MgSO$_4$). Evaporation of the $CHCl_3$ left 1.77 g. of a light yellow glass: $[\alpha]_D^{23}$+6° (c 1%,$CH_3OH$); I.R. ($CDCl_3$) 3444, 3327, 1759, 1711, 1665 cm$^{-1}$; NMR ($CDCl_3$) $\delta$1.19 d (J=6.6 Hz) ($C_6'$—$CH_3$), 2.92 (N$CH_3$), 3.47 (O$CH_3$).

C. 1,2', 6'-Tri-N-benzyloxycarbonyl-2-epi-fortimicin B 4,5-carbamate and 2',6'-di-N-benzyloxycarbonyl-2-epifortimicin B 1,2;4,5-biscarbamate A magnetically stirred solution of 0.427 g. of 1,2',6'-tri-N-benzyloxycarbonyl-2-O-methanesulfonylfortimicin B-4,5-carbamate, 0.116 g. of ammonium acetate, 3 ml of water, and 6 ml of 1,2-dimethoxyethane was heated under reflux for 21 hours. The resulting solution was cooled and poured into 100 ml of 5% aqueous sodium bicarbonate. The aqueous suspension was extracted twice with 50 ml portions of chloroform. The chloroform extracts were combined and dried over anhydrous magnesium sulfate. Evaporation of the chloroform under reduced pressure left 0.386 mg of a mixture of products.

A sample of 3.01 g of the mixture of products was chromatographed on a column of 250 g of silica gel packed and eluted with a solvent system composed of ethyl acetate, 1,2-dichloroethane[9:1(v/v)]. Initial fraction gave 1.24 g of 1,2',6'-tri-N-benzyloxycarbonyl-2-epi-fortimicin B-4,5-carbamate: $[\alpha]_D^{21}$+8.5°(c 1%,$CH_3OH$); I.R. ($CDCl_3$) 3442, 3328(shoulder), 1743, 1698 cm$^{-1}$; NMR($CDCl_3$) $\delta$1.05 d($C_6'$—$CH_3$,$J_{5',6'}$=6.2 Hz), 2.83(N$CH_3$),3.43(O$CH_3$). Anal. Calcd. for $C_{40}H_{48}N_4O_{12}$: C,61.48; H,6.23; N,7.21. Found: C,61.64; H,6.37; N,7.25.

Further elution of the column gave 0.965 g of 2',6'-di-N-benzyloxycarbonyl-2-epi-fortimicin B-1,2:4,5-biscarbamate: $[\alpha]_D^{21}$+7.3°(c 1%, $CH_3OH$); I.R. ($CDCl_3$) 3443,3323,1749,1699 cm$^{-1}$; NMR($CDCl_3$) $\delta$1.17 d ($C_6'$—$CH_3$, $J_{5',6'}$=6.8 $H_z$), 2.94(N$CH_3$), 3.52(O$CH_3$).

D. 2-epi-Fortimicin B-1,2:4,5-biscarbamate dihydrochloride

2',6'-Di-N-benzyloxycarbonylfortimicin B-1,2:4,5-biscarbamate(1.0 g) in 30 ml of 0.4 N hydrochloric acid in methanol was hydrogenated for 4 hours under 3 atmospheres of hydrogen in the presence of 1 g. of 5% Pd on carbon. The catalyst was removed by filtration and the solvent was evaporated under reduced pressure. Residual hydrochloric acid was removed by codistillation with methanol under reduced pressure leaving 0.717 g of product as a white glass: $[\alpha]^{22}$+36°(c 1%, $CH_3OH$); I.R. (KBr) 1738, 1723 cm$^{-1}$; NMR($D_2O$) $\delta$1.79($C_6'$—$CH_3$,$J_{5',6'}$= Hz), 3.42(N$CH_3$),4.04(O$CH_3$), 5.56 d($H_{1'}$, J=3.6 Hz); MS:M+ Calcd. for $C_{17}H_{28}N_4O_7$: 400.1958. Meas. 400.1933.

E. 2-epi-Fortimicin B

A solution of 4.94 g of 2-epi-fortimicin B-1,2:4,5-biscarbamate dihydrochloride was heated at 75° C. for 66 hours. The resulting solution was cooled, brought to pH 7 with 1 N hydrochloric acid, and evaporated to dryness under reduced pressure. The residue was treated with several portions of boiling ethanol, and the resulting suspension filtered. Evaporation of the ethanol left 4.12 g of glass. The product was chromatographed on a column of 450 g of silica gel packed and eluted with a solvent system composed of chloroform-methanol-ammonium hydroxide(concentrated)-water [10:10:1:1(v/v/v/v)] to yield 3.0 g of 2-epi-fortimicin B: $[\alpha]_D^{23}$+77.8°(c 1%, $CH_3OH$); NMR($D_2O$)$\delta$1.50 d($C_6'$—$CH_3$, $J_{5',6'}$=6.8 Hz), 2.83(N$CH_3$), 3.99(O$CH_3$), 5.38 d($C_{1'}$—H, $J_{1',2'}$=3.4 Hz).

F. 3-O-Demethyl-2-epi-fortimicin B

3-O-Demethyl-2-epi-fortimicin B was prepared according to the method of Example 2, using 2-epi-fortimicin B in place of fortimicin B.

EXAMPLE 7

3-O-Demethyl-2-epi-fortimicin A

A. 1,2',6'-Tri-N-benzyloxycarbonyl-2-epi-fortimicin B

To a magnetically stirred solution of 2.9 g of 2-epi-fortimicin B, 42 ml of water and 84 ml of methanol, cooled in an ice bath, was added 6.4 g of N-benzyloxycarbonyloxysuccinimide. Stirring was continued with cooling for 3 hours and then at ambient temperature overnight. The resulting solution was shaken with a mixture of chloroform and 5% aqueous sodium bicarbonate. The chloroform solution was separated and the aqueous solution extracted with two portions of chloroform. The chloroform solutions were combined and dried over magnesium sulfate. Evaporation of chloroform under reduced pressure left 6.91 g of a glass which was chromatographed on a column of 450 g of silica gel packed and eluted with a solvent system composed of 1,2-dichloroethane-ethanol[9:1(v/v)] to yield 3.1 g of product: $[\alpha]_D^{23}+59°$ (c 1%, $CH_3OH$); I.R. ($CDCl_3$) 3440,3330, 1708 cm$^{-1}$.

B. 1,2',6'-Tri-N-acetylfortimicin B

A magnetically stirred mixture of 33.4 g of tetra-N-acetylfortimicin B, prepared according to the method of Egan et al., *J. Antibiotics*, No. 7, 552(1977), 20 g of sodium bicarbonate, 300 ml of water and 1 liter of methanol was heated under reflux overnight. The major portion of the solvent was evaporated under reduced pressure, and residual water was removed by codistillation with several portions of ethanol under reduced pressure. The residue was triturated with several portions of warm chloroform. The supernatant was filtered and evaporated to dryness under reduced pressure leaving 21.9 g of crude material which was chromatographed on a column of 400 mg of silica gel, packed and eluted with a solvent system composed of chloroform-95% aqueous methanolammonium hydroxide (concentrated) [18:6:0.5(v/v/v)] to yield 4.37 g of pure product: $[\alpha]_D^{21.2}+27.8°$ (c 1%, $CH_3OH$); I.R. ($CDCl_3$) 3553,3439,3333,1655 cm$^{-1}$.

C. 1,2',6'-Tri-N-acetyl-4-N-ethoxycarbonylfortimicin B

A magnetically stirred solution of 0.6128 g of 1,2',6'-tri-N-acetylfortimicin B, 0.270 ml of ethyl chloroformate and 30 ml of methanol was stirred at room temperature for 4.5 hours. Solid sodium bicarbonate (0.4271 g) was added and stirring was continued for 1 hour. The resulting suspension was filtered, and the filtrate was evaporated to dryness under reduced pressure. The residue was washed with chloroform, and the supernatant was filtered and evaporated to dryness leaving 628.8 mg of a white glass. The latter was chromatographed on a column of 60 g of silica gel packed and eluted with a solvent system composed of chloroform-methanol[9:1(v/v)] to yield 378.4 mg of product: I.R. ($CDCl_3$) 3537, 3337, 1657 cm$^{-1}$.

D. 1,2',6'-Tri-N-acetylfortimicin B-4,5-carbamate

A solution prepared from 0.3473 g of 1,2',6'-tri-N-acetyl-4-N-ethoxycarbonylfortimicin B, 0.4184 g of 1,5-diazabicyclo[5.4.0]undecene-5 and 20 ml of benzene was heated under reflux for five days. The benzene was evaporated and the residue was chromatographed on a column of 60 g of silica gel packed and eluted with a solvent system composed of chloroform-methanol[87:13(v/v)] to yield 0.2792 g of 1,2',6'-tri-N-acetylfortimicin B-4,5-carbamate:I.R.($CDCl_3$) 3533,3440,3402,3315,1753 and 1658 cm$^{-1}$.

E. 2',6'-Di-N-acetyl-2-epi-fortimicin B-1,2-(2-methyl)oxazoline-4,5-carbamate To a magnetically stirred solution of 5.09 g of 1,2',6'-tri-N-acetylfortimicin B-4,5-carbamate in 50 ml of pyridine, cooled in an ice bath, was added 3.50 g of methanesulfonic anhydride. Stirring was continued with cooling for 1 hour and then at ambient temperature overnight. The resulting mixture was shaken with a mixture of 5% aqueous sodium bicarbonate and chloroform. The chloroform solution was separated and the aqueous solution was again extracted with chloroform. The chloroform solutions were combined and dried over magnesium sulfate. Evaporation of the chloroform left 4.47 g of product: I.R. ($CDCl_3$) 3443,3321,1746,1649 cm$^{-1}$.

F. 1,2',6'-Tri-N-acetyl-2-epi-fortimicin B-4,5-carbamate

A magnetically stirred solution of 4.4.0 g of the above-prepared compound, 45 ml of 0.4 N HCl and 180 ml of tetrahydrofuran was kept at room temperature for 0.5 hours. Sodium bicarbonate solution (150 ml, 5% aqueous) was added. The major portion of the solvent was evaporated under reduced pressure and residual water was removed by co-distillation with ethanol under reduced pressure. The residue was triturated with 400 ml of boiling water. The supernatant was filtered and the chloroform-insoluble residue was washed several times with fresh chloroform. The washings were filtered, the chloroform solutions combined and the chloroform evaporated under reduced pressure leaving 4.66 g of a glass. The latter was chromatographed on a column of silica gel packed and eluted with a solvent system composed of dichloromethane-methanol[9:1(v/v)] to yield 3.64 g of product: I.R. ($CDCl_3$) 3439,3320,1752 and 1652 cm$^{-1}$.

G. 1,2',6'-Tri-N-acetyl-2-O-benzyl-2-epi fortimicin B-4,5-carbamate

To a magnetically stirred suspension of 2.67 g of 1,2',6'-tri-N-acetyl-2-epi-fortimicin B-4,5-carbamate, 2.22 g of BaO and 2.86 g of barium hydroxide.8H$_2$O in 134 ml of N,N-dimethylformamide, cooled in an isopropanol ice bath, were added 2.3 ml of benzylbromide. The reaction mixture was stirred in the isopropanol ice bath for 15 minutes and then stirred in an ice bath for 3.5 hours, and then stirred at ambient temperature overnight. The mixture was filtered through a celite mat. The mat was washed thoroughly with chloroform, the filtrates combined and the solvent evaporated under reduced pressure. The residue was taken up in chloroform and the chloroform mixture was again filtered through a celite mat. The solvent was evaporated under reduced pressure and residual N,N-dimethylformamide was removed by codistillation with toluene under reduced pressure leaving 3.00 g of an oil. The latter was chromatographed on a column of 250 g of silica gel packed and eluted with a solvent system composed of 1,2-dichloroethane-methanol[9:1(v/v)] to yield 1.83 g of product: $[\alpha]_D^{23.2}+52.5°$ (c 1%,$CH_3OH$); I.R. ($CDCl_3$) 3439,3312,1742,1644 cm$^{-1}$.

H. 2-O-Benzyl-2-epi-fortimicin B

A solution of 6.39 g of 1,2',6'-tri-N-acetyl-2-O-benzyl-2-epi-fortimicin B-4,5-carbamate in 800 ml of 2 N aqueous sodium hydroxide was heated at 85° C. for three days. The resulting solution was cooled to room temperature and brought to pH 7 by the addition of 1 N hydrochloric acid. The water was evaporated under reduced pressure and residual water removed by co-distillation with ethanol under reduced pressure. The residue was treated with several portions of boiling chloroform and the supernatants were filtered and combined. Evaporation of the chloroform left 5.53 g of a glass. The latter product was chromatographed on a column of 450 g of silica gel packed and eluted with a solvent system composed of dichloromethane-methanol-concentrated ammonium hydroxide [10:1:1(v/v/v)] to yield 3.24 g of product:I.R.(CDCl$_3$) 3372,3292, cm$^{-1}$.

I.
1,2',6'-Tri-N-benzyloxycarbonyl-2-O-benzyl-2-epi-fortimicin B

To a magnetically stirred solution of 2.51 g of 2-O-benzyl-2-epi-fortimicin B, 28 ml of water and 10 ml of chloroform, cooled in an ice bath, were added 4.4 g of N-benzyloxycarbonyloxysuccinimide. Stirring was continued with cooling for 3 hours and then at ambient temperature overnight. The resulting solution was poured into 5% aqueous sodium bicarbonate and the resulting suspension was extracted with several portions of chloroform. The chloroform solutions were combined and dried over magnesium sulfate. Evaporation of the chloroform left 4.64 g of glass. A sample of 0.998 g of this material was chromatographed on a column of 100 g of silica gel packed and eluted with a solvent system composed of ehtyl acetate-triethylamine [19.8:0.2(v/v)] to yield 0.584 g of product; $[\alpha]_D^{23.2}+37.2°$ (c 1%, CH$_3$OH); I.R. (CDCl$_3$) 3444,3347,1704 cm$^{-1}$.

J.
Tetra-N-benzyloxycarbonyl-2-O-benzyl-2-epi-fortimicin A

To a magnetically stirred solution of 0.500 g of 1,2',6'-tri-N-benzyloxycarbonyl-2-O-benzyl-2-epi-fortimicin B in 30 ml of tetrahydrofuran, cooled in an ice bath, was added 0.182 g of N-(benzyloxycarbonyloxyglycyl)succinimide. Stirring was continued with cooling for 3 hours and then at ambient temperature overnight. The resulting solution was poured into a solution of 5% aqueous sodium bicarbonate, and the suspension was extracted with several portions of chloroform. The chloroform solutions were combined and dried over magnesium sulfate. Evaporation of the chloroform left 0.607 g of glass. The latter product (0.600 g) was chromatographed on a column of 60 g of silica gel packed and eluted with a solvent system composed of 1,2-dichloroethane-ethyl acetate[1:1(v/v)] to yield 0.413 g of product: I.R. (CDCl$_3$) 3433, 3335, 1710, 1640 cm$^{-1}$.

K. 2-epi-Fortimicin A tetrahyrochloride

Tetra-N-benzyloxycarbonyl-2-O-benzyl-2-epi-fortimicin A was hydrogenated for 4 hours in 100 ml of 0.2 N hydrochloric acid in methanol under 3 atmospheres of hydrogen in the presence of 2.5 g of 5% palladium on carbon. The catalyst was removed by filtration and the solvent was evaporated under reduced pressure. Residual hydrochloric acid was removed by co-distillation with methanol under reduced pressure to yield 0.668 g of 2-epi-fortimicin A tetrahydrochloride:$[\alpha]_D^{22}+55°$ (c 1%, CH$_3$OH); I.R.(KBr) 1640 cm$^{-1}$.

L. 3-O-Demethyl-2-epi-fortimicin A disulfate

3-O-Demethyl-2-epi-fortimicin A disulfate was prepared according to the method of Example 4 from 248 mg of 2-epi-fortimicin A tetrahydrochloride in twenty percent yield: Mass Spec. (MS 5209): M+ obsd. C$_{16}$H$_{33}$N$_5$O$_6$ requires 311.2431, measd. 319.2422; PMR(D$_2$O) δ1.76d(C$_6$'—CH$_3$, J$_{5',6'}$=6.5 Hz), 3.58s(NCH$_3$), 5.76 d(C$_{1'}$—H,J$_{1',2'}$=3.0 Hz). The sulfate salt was prepared by passage of the base through a column of ion exchange resin(NH$_4$+ form) to remove the chloride ion and worked up with sulfuric acid.

EXAMPLE 8

3-O-Demethyl-2'-N-glycylfortimicin A disulfate

3-O-Demethyl-2'-N-glycylfortimicin A disulfate was (239 mg, 0.52 mmole) (prepared according to U.S. Pat. No. 4,187,298, according to the method of Example 7: Mass Spec: M+ obsd. C$_{18}$H$_{36}$N$_6$O$_7$ requires 448.2646, measd. 448.2625; PMR (D$_2$O); δ 1.76 d(C$_6$'—CH$_3$,J$_{5',6'}$=6.5 Hz), 3.57s(NCH$_3$), 5.50d(C$_{1'}$—H,J$_{1',2'}$=3.0 Hz).

EXAMPLE 9

3-O-Demethyl-6'-epi-fortimicin A disulfate

3-O-Demethyl-6'-epi-fortimicin A disulfate was prepared in 22 percent yield from 238 mg of 6'-epi-fortimicin A (U.S. Pat. No. 4,214,075, following the method of Example 7L:Mass Spec:M+ obsd. C$_{16}$H$_{33}$N$_5$O$_6$ requires 391.2431, measd. 391.2434; PMR(D$_2$O)δ 1.73,d(C$_6$'—CH$_3$,J$_{5',6'}$=7.0 Hz), 3.59s(NCH$_3$), 5.76d(C$_{1'}$—H,J$_{1',2'}$=3.2 Hz).

EXAMPLE 10

3-O-Demethyl-4-N-(L-2-hydroxy-4-aminobutyl)fortimicin B disulfate.

3-O-Demethyl-4-N-(L-2-hydroxy-4-aminobutyl)fortimicin B disulfate was prepared in 22 percent yield according to the method of Example 7L. from 4-N-(L-2-hydroxy-4-aminobutyl)fortimicin B (249 mg, 0.59 mmole) (U.S. Pat. No. 4,091,032, issued May 23, 1978). Mass Spec. (M+1)+ obsd. C$_{18}$H$_{40}$N$_5$O$_6$ requires 422.2979,measd. 422.2964; PMR(D$_2$O)δ 1.76 d(C$_6$'—CH$_3$,J$_{5',6'}$=7.0 Hz), 3.58s(NCH$_3$), 5.83d(C$_{1'}$—H,J$_{1',2'}$=3.2 Hz).

EXAMPLE 11

2-Amino-3-O-demethyl-2-deoxyfortimicin A disulfate

2-Amino-3-O-demethyl-2-deoxyfortimicin A disulfate was prepared in eleven percent yield from 2-amino-2-deoxyfortimicin A, (240 mg, 0.59 mmole), (prepared as described in Example 12), by the method of Example 7L: Mass Spec. M+ obsd. C$_{16}$H$_{34}$N$_6$O$_5$ requires 390.2591, measd. 390.2568; PMR(D$_2$O)δ 1.77d(C$_6$'—CH$_3$,J$_{5',6'}$=6.7 Hz), 3.59s (NCH$_3$), 5.78d(C$_{1'}$—H,J$_{1',2'}$=3.0 Hz).

EXAMPLE 12

2-Amino-2-deoxyfortimicin A

A solution of 1.160 g of 1,2-epiminofortimicin A(U.S. Pat. No. 4,192,867) and 72 ml of a saturated solution of aqueous sodium azide was adjusted to pH 5.0 with hydrochloric acid. After standing at room temperature for 60 hours, the solution was concentrated to dryness under reduced pressure. The residue was passed through a column (2.2×100 cm) of Sephadex G-15

(sold by Pharmacia Fine Chemicals, Inc.) prepared and eluted with 0.1 N acetic acid. Elutes containing the major component are collected and taken to dryness to leave 0.446 g of residue. The residue was rapidly chromatographed on a column (1.8×41 cm) of silica gel prepared and eluted with a solvent system consisting of the lower phase of a mixture of chloroform-methanol-concentrated ammonium hydroxide [1:1:1(v/v/v)]. Fractions containing only the major components were taken to dryness and the residue was dissolved in 50 ml of 0.2 N hydrochloric acid in methanol. The solution was evaporated to dryness and excess hydrochloric acid was removed by repeated co-distillation with methanol to yield 0.381 g of 2-azido-2-deoxyfortimicin A tetrahydrochloride: I.R. (KBr) 3420,1640,1595 and 1490 cm$^{-1}$.

A solution prepared from 0.174 g of 2-azido-2-deoxyfortimicin A and 40 ml of 0.2 N hydrochloric acid in methanol was hydrogenated over 0.20 g of palladium on carbon for 4 hours. The catalyst was collected on a filter and washed with methanol. The filtrate was concentrated to dryness and the excess hydrochloric acid was removed by repeated codistillation with methanol under reduced pressure to give 0.157 go of 2-amino-2-deoxyfortimicin A pentahydrochloride: I.R. (KBr) 3410,2930,1645,1590 and 1486 cm$^{-1}$.

EXAMPLE 13

3-O-Demethyl-6′-N-methylfortimicin A disulfate

3-O-Demethyl-6′-N-methylfortimicin A disulfate was prepared according the the method of Example 7 L. in thirty five percent yield from 263 mg of 6′-N-methylfortimicin A (U.S. Pat. No. 4,205,470. Mass Spec:M+ obsd. $C_{17}H_{35}N_5O_6$ requires 405.2587, measd. 405.2584; PMR(D$_2$O) δ1.79d, (C$_6$'—CH$_3$,J$_{5',6'}$=6.8 Hz),3.17s(C$_6$'—NCH$_3$), 3.58s(C$_4$—NCH$_3$), 5.77d (C$_1$'—H,J$_{1',2'}$=3.0 Hz).

EXAMPLE 14

3-O-Demethyl-2-deoxy-4-N-β-aminoethylfortimicin B

3-O-Demethyl-2-deoxy-4-N-β-aminoethylfortimcin B disulfate was prepared according to the method of Example 7 L. in twenty two percent yield from 199 mg of 2-deoxy-4-N-β-aminoethylfortimicin B(U.S. Pat. No. 4,205,470. Mass Spec.M+ obsd. $C_{16}H_{36}N_5O_4$ requires 362.2767, measd. 362.2776; PMR(D$_2$O):δ 1.76d (C$_6$'—CH$_3$,J$_{5',6'}$=6.8 Hz), 3.50s(NCH$_3$), 5.87d(C$_1$'—H,J$_{1',2'}$=3.8 Hz); CMR(D$_2$O,pD 5.17):95.6, 73.7, 71.0, 68.3, 67.9, 67.4, 53.0, 51.7, 50.0, 49.2, 40.0, 35.9, 28.5, 26.3, 21.5, 15.1.

EXAMPLE 15

3-O-Demethyl-1-epi-2-deoxyfortimicin A disulfate

3-O-Demethyl-1-epi-2-deoxyfortimicin A disulfate was prepared in twenty percent yield from 29 mg of 1-epi-2-deoxyfortimicin A free base(Derwent DT2813-021) by the method of Example 7L.: Mass Spec M+obsd. 375.2475. $C_{16}H_{33}N_5O_5$ requires 375.2582; PMR(D$_2$O) δ 1.75d(C$_6$'—CH$_3$,J$_{5',6'}$=6.6 Hz), 3.55s (NCH$_3$), 5.92d(C$_1$'—H, J$_{1',2'}$=3.0 Hz).

Novel compounds prepared according to the process of the present invention are represented by the formula:

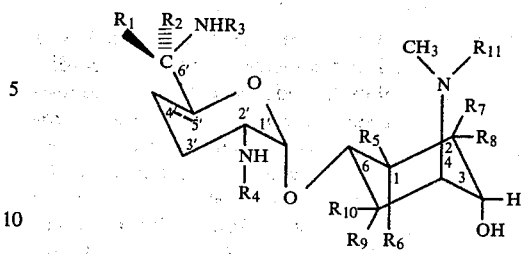

wherein: $R_1$ and $R_2$ are hydrogen or methyl with the limitation that one of either $R_1$ or $R_2$ must be hydrogen; $R_3$ is hydrogen or methyl; $R_4$ and $R_{11}$ are the same or different members of the group consisting of hydrogen, acyl, aminoacyl, diaminoacyl, N-loweralkylaminoacyl, N,N-diloweralkylaminoacyl, hydroxy-substituted aminoacyl, loweralkyl, aminoloweralkyl, diaminoloweralkyl, hydroxyloweralkyl, N-loweralkylaminoloweralkyl, N,N-diloweralkylaminoloweralkyl, N-loweralkylaminohydroxyloweralkyl, and N,N-diloweralkylaminohydroxyloweralkyl; $R_5$ and $R_6$ are hydrogen or amino with the limitation that one of either $R_5$ and $R_6$ must be hydrogen; $R_7$ and $R_8$ are selected from the group consisting of hydrogen, hydroxy, amino and chloro with the limitation that one of either $R_7$ or $R_8$ must be hydrogen; $R_9$ and $R_{10}$ are hydrogen or hydroxy with the limitation that one of either $R_9$ and $R_{10}$ must be hydrogen; excluding compounds wherein $R_1$ is hydrogen, $R_2$ is methyl, $R_3$ is hydrogen, $R_5$ is amino, $R_8$ is hydroxy and $R_{10}$ is hydrogen when position 4′-5′ is saturated; and excluding all $C_4$ and $C_{2'}$ derivatives when $R_1$ is hydrogen, $R_2$ is methyl, $R_3$ is hydrogen, $R_5$ is amino, $R_8$ is hydroxy and $R_{10}$ is hydroxy when position 4′-5′ is saturated; and the pharmaceutically acceptable salts thereof.

The term "acyl", as used herein, refers to acyl radicals of loweralkylcarboxylic acids represented by the formula

wherein R is loweralkyl, i.e., acetyl, propionyl, butryl, valeryl, etc.

The terms aminoacyl, hydroxy-substituted aminoacyl, etc. enumerated in the definitions for $R_4$ and $R_{11}$ include, but are not limited to, as will be obvious to one skilled in the art, to naturally occuring amino acids such as glycyl, valyl, analyl, sarosyl, leucyl, isoleucyl, prolyl, seryl and like amino acids as well as groups such as 2-hydroxy-4-aminobutyryl, etc. The amino acid residues, with the exception of glycyl, can be either in the L- or D-configurations or mixtures thereof.

The term "loweralkyl", as used herein, refers to straight or branched chain alkyl radicals containing from 1 to 6 carbon atoms, inclusive and includes, but is not limited to, methyl, ethyl, n-propyl, iso-propyl, n-butyl, iso-butyl, tert-butyl, n-pentyl, 1-methylbutyl, 2,2-dimethylpropyl, n-hexyl, 2-methylpentyl, and the like.

The substituted alkyl groups are well known in the art and include, for example, aminomethyl, β-aminoethyl, N-methylaminoethyl, N,N-dimethylaminopropyl, hydroxyethyl, 2-hydroxy-4-aminobutyl, etc.

The term "pharmaceutically acceptable salts" refers to the non-toxic acid addition salts of compounds of this invention which can be prepared either in situ during the final isolation and purification or by separately reacting the free base with a suitable organic or inorganic acid by methods well known in the art. Representative salts include the mono, di, tri, tetra or other per salts such as the hydrochloride, hydrobromide, sulfate, bisulfate, tetrahydrochloride, pentahydrochloride, acetate, oxalate, valerate, oleate, palmitate, stearate, laurate, borate, benzoate, lactate, phosphate, tosylate, citrate, maleate, fumarate, succinate, tartrate, napsylate and like salts and per salts.

The compounds of this invention are useful as antibacterial agents against susceptible or sensitive strains of gram-negative and gram positive bacilli such as *Staphylococcus aureus, Escherichia coli, Pseudomonas aeruginosa Bacillus subtilis, Proteus vulgaris, Shigella sonnei, Salmonella typhi,* and *Klebsiella pneumoniae.*

The term "sensitive or susceptible strains" refers to strains of bacilli or organisms which have been demonstrated to be sensitive to a particular antibiotic in a standard in vitro sensitivity test and thus in vitro activity has been established for a particular antibiotic against a specific strain of a specific organism.

The compounds of this invention are administered parenterally, i.e., intravenously, intramuscularly, intraperitoneally or subcutaneously for systemic effect in daily dosages of from 20 to 80 mg/kg daily, preferably from about 25 to about 60, and most preferably from about 25 to 30 mg/kg of body weight daily, based on lean body weight as is good medical practice with the aminoglycoside antibiotics. It is preferred to administer the compounds of this invention in divided dosages, i.e. three to four times daily. The compounds can also be administered orally at the above dosages to sterilize the intestinal tract and can be further administered in suppository form.

In addition, the compounds can be incorporated into antibacterial solutions and used to sterilize laboratory benchtops, operating room surfaces and the like.

Preparations according to the present invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions and the like. They can also be manufactured in the form of sterile solid compositions which can be dissolved in sterile water of some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, i.e. lubricating agents such as magnesium stearate. In the case of capsules, tablets and pills, the dosage forms may also comprise buffering agents. Tablets and pills can additionally be prepared with enteric coatings.

Liquid dosage forms for oral administration also include pharmaceutically acceptable emulsions, solutions, suspensions, syrups and elixirs containing inert diluents commonly used in the art, such as water. Besides the inert diluents, the compositions of this invention can also include adjuvants such as wetting agents, emulsifying agents and suspending agents, as well as sweetening and perfuming agents.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment.

It will be apparent to those skilled in the art that the above examples are for the purpose of illustration and do not limit the present invention. Compounds represented by the above formula are readily prepared from the corresponding 3-methyl-compound, free base, according to the method set forth herein.

Turning again to the method of this invention, while it is preferred to cool the antibiotic solution prior to reacting it with a boron trihalide in order to dispel the heat of reaction, it has been found that the reaction can be conducted at temperatures of from between −72° to 100° C., preferrably from about 15° to about room temperature or 23° C. and in those instances where the heat of reaction is to be dispelled, most preferrably from about 0° C. to about 5° C.

Depending upon the temperature, the reaction is conducted from 30 minutes to 48 hours, and preferably from 24 to 48 hours.

I claim:

1. An improved method of O-demethylating an aminoglycoside antibiotic which is not highly acid labile containing an O-demethyl group in the cyclitol moiety comprising the steps of dissolving the aminoglycoside antibiotic to be O-demethylated in an inert solvent, reacting the resulting solution with a boron trihalide at a temperature of between −72° C. to 100° C., for a time sufficient to complete the reaction, and thereafter recovering the O-demethylated antibiotic from the reaction mixture.

2. The method of claim 1 wherein said boron trihalide is selected from the group consisting of boron tribromide, boron trichloride and boron triiodide.

3. The method of claim 1 or 2 wherein the antibiotic to be O-demethylated is reacted as the free base.

4. The method of claim 1 or 2 wherein said boron trihalide is boron tribromide.

5. The method of claim 1 wherein said antibiotic is a fortimicin antibiotic.

6. The method of claim 1 wherein said solvent is methylene chloride.

7. The method of claim 1 wherein said antibiotic solution is reacted with said boron trihalide for a period of from 30 minutes to about 48 hours.

8. The method of claim 7 wherein said boron trihalide is selected from the group consisting of boron tribromide, boron trichloride and boron triiodide.

9. The method of claim 8 wherein said boron trihalide is boron tribromide.

10. The method of claim 1 wherein said reaction is conducted at a temperature of between −15° to 23° C.

11. The method of claim 1 wherein said reaction is conducted at a temperature of between 0° to B 5° C.

12. The method of claim 2 or 5 wherein said reaction is conducted at a temperature of between −15° to 23° C.

13. The method of claim 2 or 5 wherein said reaction is conducted at a temperature of between 0° to 5° C.

14. The method of claim 1 wherein said antibiotic is fortimicin A.

15. The method of claim 1 wherein said antibiotic is fortimicin B.

16. The method of claim 1 wherein said antibiotic is 2-deoxy-fortimicin A.

17. The method of claim 1 wherein said antibiotic is 1-epi-fortimicin A.

18. The method of claim 1 wherein said antibiotic is 2-epi-fortimicin A.

19. The method of claim 1 wherein said antibiotic is 5-deoxyfortimicin A.

20. The method of claim 1 wherein said antibiotic is 2,5-dideoxyfortimicin A.

21. The method of claim 1 wherein said antibiotic is 2'-N-glycylfortimicin A.

22. The method of claim 1 wherein said antibiotic is 6'-epi-fortimicin A.

23. The method of claim 1 wherein said antibiotic is 4-N-(L-2-hydroxy-4-aminobutyl)fortimicin B.

24. The method of claim 1 wherein said antibiotic is 2-amino-2-deoxyfortimicin A.

25. The method of claim 1 wherein said antibiotic is 6'-N-methylfortimicin A.

26. The method of claim 1 wherein said antibiotic is 2-deoxy-4-N-beta-aminoethylfortimicin B.

27. A 3-O-demethylfortimicin represented by the formula:

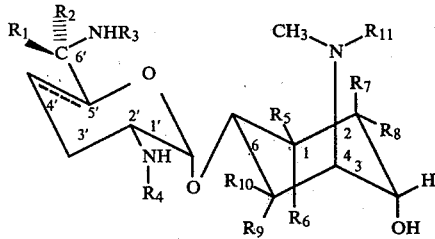

wherein: $R_1$ and $R_2$ are hydrogen or methyl with the limitation that one of either $R_1$ or $R_2$ must be hydrogen; $R_3$ is hydrogen or methyl; $R_4$ and $R_{11}$ are the same or different members of the group consisting of hydrogen, acyl of the formula

wherein $R_{12}$ is loweralkyl, aminoacyl, diaminoacyl, N-loweralkylaminoacyl, N,N-diloweralkylaminoacyl, hydroxy-substituted aminoacyl, loweralkyl, aminoloweralkyl, diaminoloweralkyl, hydroxyloweralkyl, N-loweralkylaminoloweralkyl, N,N-diloweralkylaminoloweralkyl, N-loweralkylaminohydroxyloweralkyl, and N,N-diloweralkylaminohydroxyloweralkyl; $R_5$ and $R_6$ are hydrogen or amino with the limitation that one of either $R_5$ and $R_6$ must be hydrogen; $R_7$ and $R_8$ are selected from the group consisting of hydrogen, hydroxy, amino and chloro with the limitation that one of either $R_7$ or $R_8$ must be hydrogen; $R_9$ and $R_{10}$ are hydrogen or hydroxy with the limitation that one of either $R_9$ and $R_{10}$ must be hydrogen; excluding compounds wherein $R_1$ is hydrogen, $R_2$ is methyl, $R_3$ is hydrogen, $R_5$ is amino, $R_8$ is hydroxy and $R_{10}$ is hydrogen when position 4'-5' is saturated; and excluding all $C_4$ and $C_{2'}$-derivatives when $R_1$ is hydrogen, $R_2$ is methyl, $R_3$ is hydrogen, $R_5$ is amino $R_8$ is hydroxy and $R_{10}$ is hydroxy when position 4'-5' is saturated; and the pharmaceutically acceptable salts thereof.

28. A fortimicin of claim 27 wherein $R_4$ is hydrogen.

29. A fortimicin of claim 27 wherein $R_9$ and $R_{10}$ each are hydrogen.

30. A fortimicin of claim 29: 3-O-demethyl-2-deoxyfortimicin A or a pharmaceutically acceptable salt thereof.

31. A fortimicin of claim 29: 3-O-demethyl-2-deoxyfortimicin B or a pharmaceutically acceptable salt thereof.

32. A fortimicin of claim 27 wherein both $R_7$ and $R_8$ are hydrogen.

33. A fortimicin of claim 32: 3-O-demethyl-2-deoxyfortimicin A or a pharmaceutically acceptable salt thereof.

34. A fortimicin of claim 32: 3-O-demethyl-2-deoxyfortimicin B or a pharmaceutically acceptable salt thereof.

35. A fortimicin of claim 27 wherein $R_7$, $R_8$, $R_9$ and $R_{10}$ each are hydrogen.

36. A fortimicin of claim 35: 3-O-demethyl-2,5-dideoxyfortimicin A or a pharmaceutically acceptable salt thereof.

37. A fortimicin of claim 35: 3-O-de-methyl-2,5,-dideoxyfortimicin B or a pharmaceutically acceptable salt therof.

38. A fortimicin of claim 27 wherein $R_6$ is amino.

39. A fortimicin of claim 38: 3-O-demethyl-1-epi-fortimicin A or a pharmaceutically acceptable salt thereof.

40. A fortimicin of claim 38: 3-O-demethyl-1-epi-fortimicin B or a pharmaceutically acceptable salt thereof.

41. A fortimicin of claim 27 wherein $R_7$ is hydroxy.

42. A fortimicin of claim 41: 3-O-demethyl-2-epi-fortimicin A or a pharmaceutically acceptable salt thereof.

43. A fortimicin of claim 41: 3-O-demethyl-2-epi-fortimicin B or a pharmaceutically acceptable salt thereof.

* * * * *